US006776767B2

(12) United States Patent
Reinecke et al.

(10) Patent No.: US 6,776,767 B2
(45) Date of Patent: Aug. 17, 2004

(54) TRACTION DEVICE AND ASSOCIATED LIFTING MECHANISMS

(75) Inventors: Steven M. Reinecke, Minneapolis, MN (US); Allan D. Luce, Shakopee, MN (US); Mark J. Strehlke, New Germany, MN (US)

(73) Assignee: AMEI Technologies Inc., Wilmington, DE (US)

( * ) Notice: Subject to any disclaimer, the term of this patent is extended or adjusted under 35 U.S.C. 154(b) by 0 days.

(21) Appl. No.: 10/335,694

(22) Filed: Jan. 2, 2003

(65) Prior Publication Data

US 2003/0097085 A1 May 22, 2003

Related U.S. Application Data

(63) Continuation of application No. 09/875,332, filed on Jun. 5, 2001, now Pat. No. 6,533,740.
(60) Provisional application No. 60/272,821, filed on Mar. 1, 2001.

(51) Int. Cl.⁷ .................................................. A61F 5/00
(52) U.S. Cl. ............................ 602/19; 602/16; 602/32; 602/36
(58) Field of Search ............................ 602/19, 32, 36, 602/38, 60–61, 5; 606/237, 240–242; 2/311, 338, 318; 482/112

(56) References Cited

U.S. PATENT DOCUMENTS

| 1,589,670 | A | 6/1926 | Vartia | |
|---|---|---|---|---|
| 2,835,247 | A | 5/1958 | Stabholc | 128/78 |
| 3,029,810 | A | 8/1962 | Martin | 128/78 |
| 3,351,053 | A | 11/1967 | Stuttle | 128/78 |
| 3,420,230 | A | 1/1969 | Ballard | 128/75 |

(List continued on next page.)

FOREIGN PATENT DOCUMENTS

| DE | 2637244 A1 | 6/1977 | ............ A61H/1/02 |
|---|---|---|---|
| DE | 19610018 A1 | 10/1996 | ............ A61F/5/042 |
| EP | 0864308 A1 | 9/1998 | ............. A61F/5/02 |
| WO | WO 02/069858 A1 | 12/2002 | ............. A61F/5/02 |

OTHER PUBLICATIONS

PCT, Notification of Transmittal of the International Search Report or the Declaration, 6 pages, Jan. 31, 2003.
Unknown, "Office, Computer and Industrial Ergonomics," AliMed, Dedham, Massachusetts, 2 page brochure, 1993.
Unknown, "1992 Catalog," The Saunders Group, Inc., brochure, 2 pages, 1992.
Unknown, "Catalog for Rehabilitation Professionals," Flaghouse Rehab., 2 pages, Undated.
Reinecke et al., "Traction Device," patent application, 09/875,486, pending, Jun. 5, 2001.
Reinecke et al., "Lifting Mechanism for a Traction Device," patent application, 09/875,332, pending, Jun. 5, 2001.

(List continued on next page.)

Primary Examiner—Danton D. DeMille
Assistant Examiner—Quang D. Thanh
(74) Attorney, Agent, or Firm—Baker & McKenzie

(57) ABSTRACT

In one embodiment, an ambulatory traction device includes a first support configured to be positioned on a user's body and a second support configured to be positioned on the user's body spaced apart from the first support such that a portion of the user's body is positioned between the first and second supports. The traction device also includes one or more lifting mechanisms that each couple the supports and apply a decompressive force to the portion of the user's body when the supports are positioned on the user's body. Each lifting mechanism includes a sleeve having a non-circular cross-section and operable to contain a fluid. Each lifting mechanism also includes a piston configured to move within the sleeve in response to an increase in pressure within the sleeve.

44 Claims, 10 Drawing Sheets

U.S. PATENT DOCUMENTS

| | | | |
|---|---|---|---|
| 3,521,623 A | 7/1970 | Nichols et al. | 128/78 |
| 3,548,817 A | 12/1970 | Mittasch | 128/75 |
| 3,598,114 A | 8/1971 | Lewis | 128/78 |
| 3,889,664 A | 6/1975 | Heuser et al. | 128/75 |
| 3,926,182 A | 12/1975 | Stabholz | 128/75 |
| 4,135,503 A | 1/1979 | Romano | 128/78 |
| 4,269,179 A | 5/1981 | Burton et al. | 128/75 |
| 4,497,517 A | 2/1985 | Gmeiner et al. | 297/231 |
| 4,552,135 A | 11/1985 | Racz et al. | 128/78 |
| 4,559,933 A | 12/1985 | Batard et al. | 128/78 |
| 4,599,998 A | 7/1986 | Castillo | 128/77 |
| 4,622,957 A | 11/1986 | Curlee | 128/78 |
| 4,682,588 A | 7/1987 | Curlee | 128/78 |
| 4,685,668 A | 8/1987 | Newlin, Jr. | 272/123 |
| 4,691,696 A | 9/1987 | Farfan de los Godos | 128/78 |
| 4,702,235 A | 10/1987 | Hong | 128/78 |
| 4,715,362 A | 12/1987 | Scott | 128/75 |
| 4,721,102 A | 1/1988 | Pethybridge | 128/78 |
| 4,836,194 A | 6/1989 | Sebastian et al. | 128/78 |
| 4,884,562 A | 12/1989 | Stone | 128/78 |
| 4,898,185 A | 2/1990 | Fuller | 128/876 |
| 4,907,575 A | 3/1990 | Satterthwaite | 128/75 |
| 4,991,572 A | 2/1991 | Chases | 128/75 |
| 4,991,573 A | 2/1991 | Miller | 128/78 |
| 5,060,640 A | 10/1991 | Rasmusson | 128/80 C |
| 5,062,414 A | 11/1991 | Grim | 128/68.1 |
| 5,111,807 A | 5/1992 | Spahn et al. | 606/244 |
| 5,144,943 A | 9/1992 | Luttrell et al. | 128/25 B |
| 5,188,586 A | 2/1993 | Castel et al. | 602/19 |
| 5,207,635 A | 5/1993 | Richards et al. | 602/19 |
| 5,256,135 A | 10/1993 | Avihod | 602/19 |
| 5,363,863 A | 11/1994 | Lelli et al. | 128/876 |
| 5,382,226 A | 1/1995 | Graham | 602/32 |
| 5,403,266 A | 4/1995 | Bragg et al. | 602/5 |
| 5,437,617 A | 8/1995 | Heinz et al. | 602/19 |
| 5,441,479 A | 8/1995 | Chitwood | 602/18 |
| 5,462,518 A | 10/1995 | Hatley et al. | 602/36 |
| 5,586,969 A | 12/1996 | Yewer, Jr. | 602/19 |
| 5,651,764 A | 7/1997 | Chiu | 602/36 |
| 5,681,267 A | 10/1997 | Molino et al. | 602/19 |
| 5,690,609 A | 11/1997 | Heinze, III | 602/19 |
| 5,722,940 A | 3/1998 | Gaylord, Jr. et al. | 602/19 |
| 5,913,410 A | 6/1999 | Tsuchiya | 2/311 |
| 5,916,188 A | 6/1999 | Ousdal | 602/32 |
| 6,099,490 A | 8/2000 | Turtzo | 602/19 |
| 6,146,345 A | 11/2000 | Mignard | 602/19 |
| 6,533,740 B2 * | 3/2003 | Reinecke et al. | 602/5 |

OTHER PUBLICATIONS

Reinecke et al., "Canting Mechanism for an Ambulatory Support Device," patent application, 09/875,473, pending, Jun. 5, 2001.

Reinecke et al., "Traction Device Adjustment Mechanism and Method," patent application, 09/875,315, pending, Jun. 5, 2001.

Reinecke et al., "Measurement Device for Fitting a Bracing Device," patent application, 10/154,695, pending, May 23, 2002.

PCT, Notification of Transmittal of the International Search Report or the Declaration, 6 pages, Apr. 7, 2002.

PCT, Notification of Transmittal of the International Search Report or the Declaration, 6 pages, Apr. 7, 2002.

PCT, Notification of Transmittal of the International Search Report or the Declaration, 7 pages, Apr. 7, 2002.

PCT, Notification of Transmittal of the International Search Report or the Declaration, 6 pages, Apr. 7, 2002.

* cited by examiner

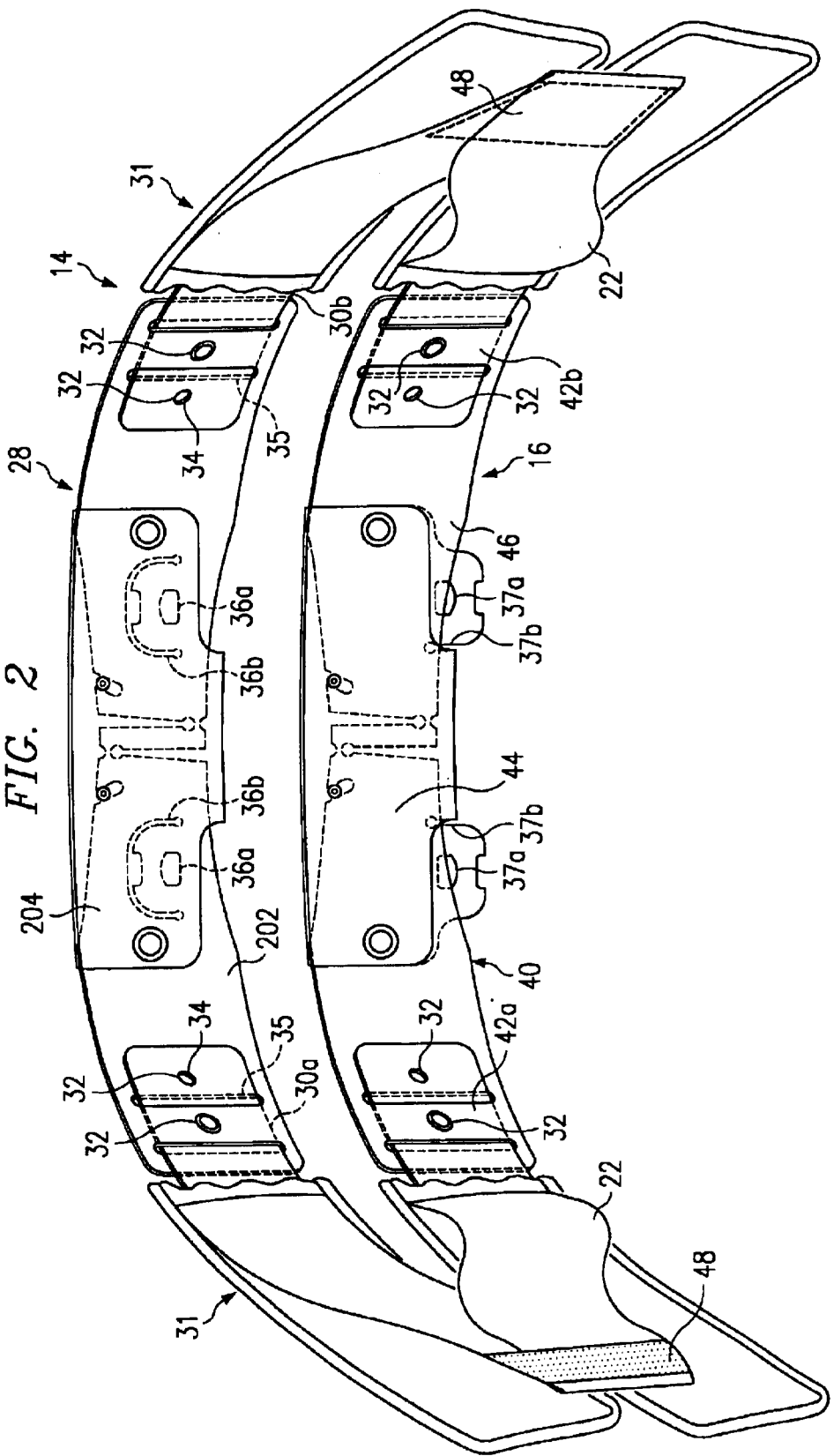

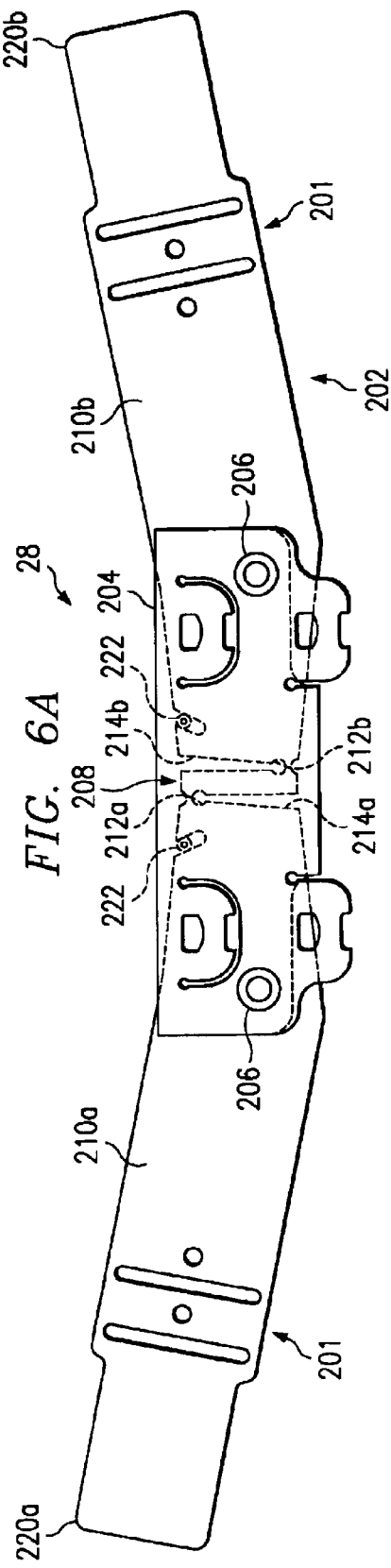
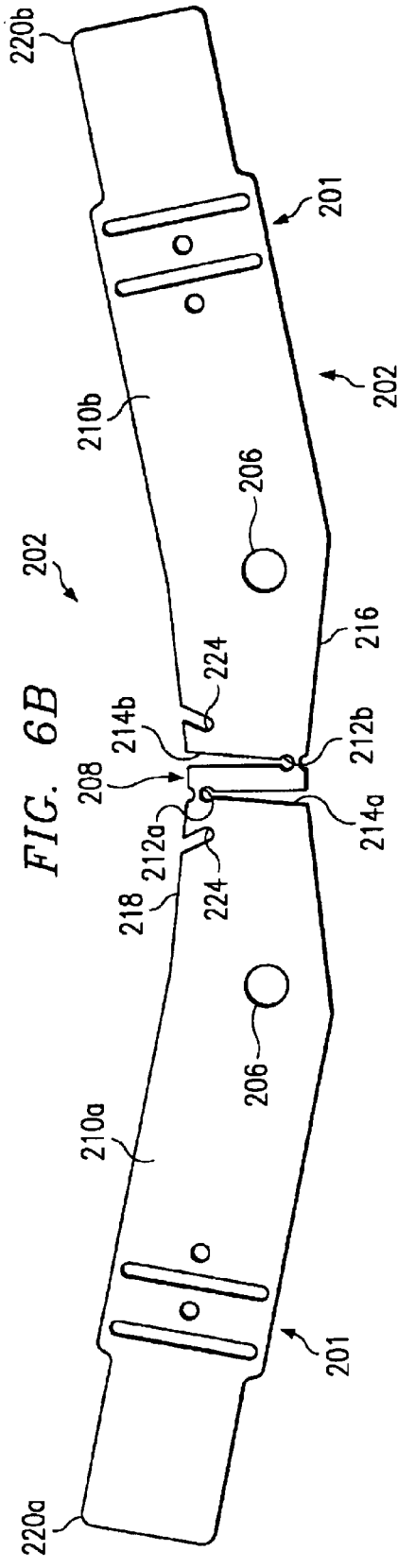

TRACTION DEVICE AND ASSOCIATED LIFTING MECHANISMS

RELATED APPLICATIONS

This application claims the benefit of Provisional Application No. 60/272,821 filed Mar. 1, 2001.

This application is a continuation of U.S. patent application Ser. No. 09/875,332 entitled "Lifting Mechanism for a Traction Device," filed Jun. 5, 2001 now U.S. Pat. No. 6,533,740 B2.

TECHNICAL FIELD OF THE INVENTION

This invention relates to the field of medical devices, and more particularly to a traction device and associated lifting mechanisms.

BACKGROUND OF THE INVENTION

Humans have long dealt with the pain, aggravation and loss of productivity arising from spinal injuries, particularly those to the low back. Most people at some point in their lives will be incapacitated by lower back pain which has become the second leading cause of pain next to headaches. The relative ease with which injuries to the spine and supporting musculature are incurred, as well as the debilitating effects of even slight injuries, merely adds to the overall severity of the problem of dealing with spinal injuries. The forms of treatment vary over the length of time that the patient experiences pain. Eighty percent of low back pain suffers will heal over six weeks with minimal intervention. However, the remaining twenty percent of sufferers create the greatest challenges and cost to the medical system. After the acute phase, surgical intervention or more invasive forms of treatment may be selected. Minimal or non-invasive treatment methods are however preferred by patients before electing to surgical methods.

SUMMARY OF THE INVENTION

According to the present invention, disadvantages and problems associated with previous medical devices for treating joints have been substantially reduced or eliminated.

In one embodiment, an ambulatory traction device includes a first support configured to be positioned on a user's body and a second support configured to be positioned on the user's body spaced apart from the first support such that a portion of the user's body is positioned between the first and second supports. The traction device also includes one or more lifting mechanisms that each couple the supports and apply a decompressive force to the portion of the user's body when the supports are positioned on the user's body. Each lifting mechanism includes a sleeve having a non-circular cross-section and operable to contain a fluid. Each lifting mechanism also includes a piston configured to move within the sleeve in response to an increase in pressure within the sleeve.

Certain embodiments of the present invention may provide one or more technical advantages. For example, certain embodiments provide a traction device that may be worn by a user to reduce the compressive forces on the user's spine by transferring the user's upper body weight off of the spine to the user's hips. In particular, the decompressive forces generated by the device may be concentrated on the lower spine of the user, an area that may be commonly injured due to compressive forces. The traction device may also provide stabilization of the torso to prevent additional compressive forces in the spine due to bending and lifting by the user. Moreover, traction devices of the present invention may be used in association with other joints of the body, such as the knee or neck. Furthermore, particular embodiments provide a traction device that is ambulatory, meaning that the device is portable and wearable during the user's daily activities. This ambulatory nature of the device provides more convenience to the user and causes less impact on the user's daily activities than previous treatment techniques.

The decompressive force applied to the user's spine (or other joint) may be applied using one or more lifting mechanisms coupled between two support belts that are wrapped around the user's torso and hips (or around other body parts, if used in association with other joints). In certain embodiments, these lifting mechanisms are piston-type lifting mechanisms that have a substantially elliptical cross-section (unlike traditional piston-type lifters, which have a circular cross-section). This substantially elliptical cross-section reduces the profile of the lifting mechanisms against the user's body thus minimizing interference with the environment while the user is performing the tasks of daily living. This low profile is more aesthetically appealing and provides more comfort to the user than would similar cylindrical lifting mechanisms. This low profile also allows the traction device to be more easily worn under other clothing, if desired.

Certain embodiments may provide all, some, or none of these advantages. Certain embodiments may provide one or more other technical advantages, one or more of which may be readily apparent to those skilled in the art from the figures, description and claims included herein.

BRIEF DESCRIPTION OF THE DRAWINGS

To provide a more complete understanding of the present invention and the features and advantages thereof, reference is made to the following description taken in conjunction with the accompanying drawings, in which:

FIG. 2 is a schematic diagram illustrating in more detail portions of example top and bottom belts of the spinal traction device of FIG. 1A;

FIGS. 6A and 6B illustrate an example back belt included in a support belt of a spinal traction device.

DESCRIPTION OF EXAMPLE EMBODIMENTS

Figure 1A:
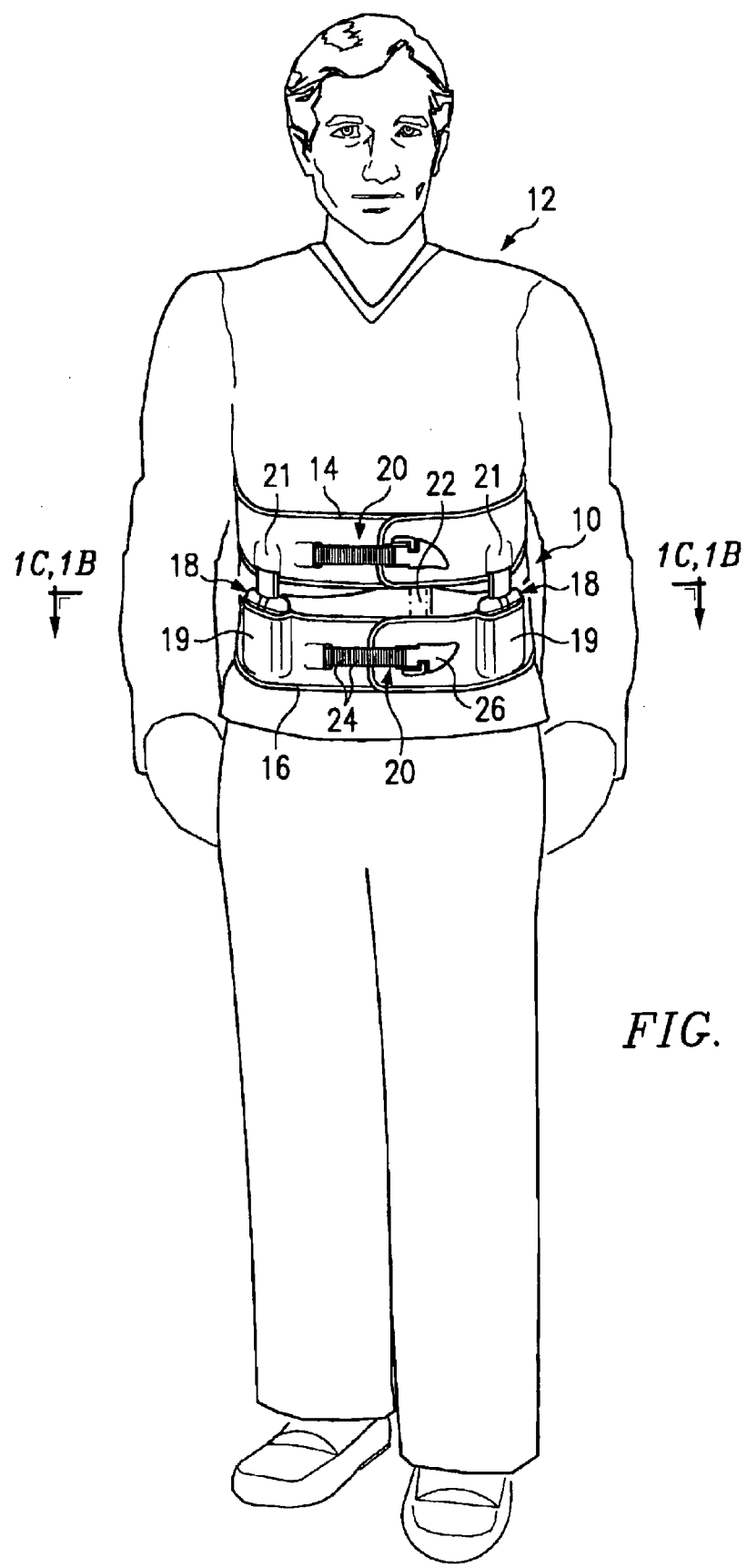
FIG. 1A is a schematic diagram showing an example spinal traction device being worn by a user.

FIG. 1A is a schematic diagram illustrating an example traction device 10 being worn by a user 12. In this embodiment, traction device 10 applies decompressive forces to the spine of user 12, which transfers body weight from the upper torso to the hips of user 12 and prevents compression and aggravation of lower back spinal conditions. In one embodiment, the offloading forces are concentrated specifically on the lower spine, rather than across the entire spine. This effect is created by decompressive forces pushing upward and downward on the lower spine. These decompressive forces are created by traction device 10, as described below. In other embodiments, tracking device 10 may also be modified to create tension in other portions of the body, such as the femur.

Spinal traction device 10 includes an upper support belt 14 and a lower support belt 16; however in other embodiments, the decompression forces may be generated through various combinations of one or more belts. Support belts 14 and 16 may be formed in any suitable manner that allows positioning around the body of a user and transferring of a decompressive force to user 12. Example details of one embodiment of belts 14 and 16 are described in greater detail below in conjunction with FIG. 2.

Spinal traction device 10 also includes one or more lifting mechanisms 18. Lifting mechanisms 18 generate a decompressive, or tensile, force that may be transferred to the spine of user 12 through support belts 14 and 16. Lifting mechanisms 18 are coupled to a valve assembly (FIG. 5) to control pressurization of lifting mechanisms 18. In one embodiment, lifting mechanisms 18 are coupled serially to the valve assembly; however, they may be coupled to the valve assembly in a parallel or other suitable fashion. Lifting mechanisms 18 are disposed within pouches 19 connected to lower support belt 16 and pouches 21 connected to upper support belt 14. Example locations about the circumference of belt 16 of lifting mechanisms 18 are shown more clearly in FIGS. 1B and 1C. Coupling of lifting mechanisms 18 to support belts 14 and 16 is described with reference to FIG. 3. Example details associated with one particular embodiment for lifting mechanism 18 are described in greater detail below in conjunction with FIGS. 4A–4D. However, in the illustrated embodiment, lifting mechanisms 18 are fluidic (for example, pneumatic or hydraulic) devices that create a decompressive, or tensile, force through fluid pressure. Lifting mechanisms 18 may also be mechanical devices. When pressurized, lifting mechanisms 18 push upward on support belt 14 and downward on support belt 16, resulting in a decompressive force on the spine of user 12.

A proper fitting of spinal traction device 10 about the body of user 12 is important. Fitting is accomplished, in part, through a pair of locking devices 20, one located on upper support belt 14 and one located on lower support belt 16 and through a common strap 22. Common strap 22 forms a part of both upper support belt 14 and lower support belt 16 and therefore allows uniform adjustment to both belts at the same time. Locking mechanisms 20 include a plurality of notches 24 and a latch 26 for locking mechanism 20 in place at a desired notch location. Locking mechanisms 20 may, however, be replaced with any suitable mechanism for locking belts 14 and 16 into a desired location, such as snaps, hook and loop type fasteners and other suitable fasteners Common strap 22 is described in greater detail below with reference to FIG. 2.

In operation, user 12 places spinal traction device 10 around his waist and adjusts belts 14 and 16 using common strap 22 to a desired tension around his waist. Common strap 22 facilitates obtaining uniform tightness of both support belts 14 and 16. User 12 may then lock belts 14 and 16 in place using locking mechanisms 26. To apply traction to the spine of user 12, a fluid is supplied to lifting mechanisms 18 to cause lifting mechanisms 18 to expand pushing belt 14 upward and belt 16 downward. Because support belts 14 and 16 are tightly wrapped around the body of user 12, this decompressive force is transferred to the user's body and hence his spine. This relieves stress on the spine.

Traction device 10 may be portable and wearable during everyday activities. Thus, device 10 may be applied at home, work, play or during travel and at user's 12 convenience. Therefore, a user is more likely to comply with therapy guidelines much more readily than if user 12 was required to travel to a clinic for therapy. The amount of force generated by the lifting mechanisms 18 may be controlled by the patient through a manual inflation device, or valve assembly, described in greater detail in conjunction with FIG. 5, or may alternatively be controlled with another suitable control device. In one embodiment, pressures generated within lifting mechanisms 18 offload approximately 50% of the body weight of user 12. A relief valve (not explicitly shown), may be provided to prevent overinflation. Such a relief valve may be situated such that user 12 may instantly relieve the pressure in lifting mechanisms 18 at any time. Spinal device 10 may also stabilize the torso, while still allowing flexibility. This stabilization prevents additional compressive forces in the spine due to bending and lifting.

Figure 1B:
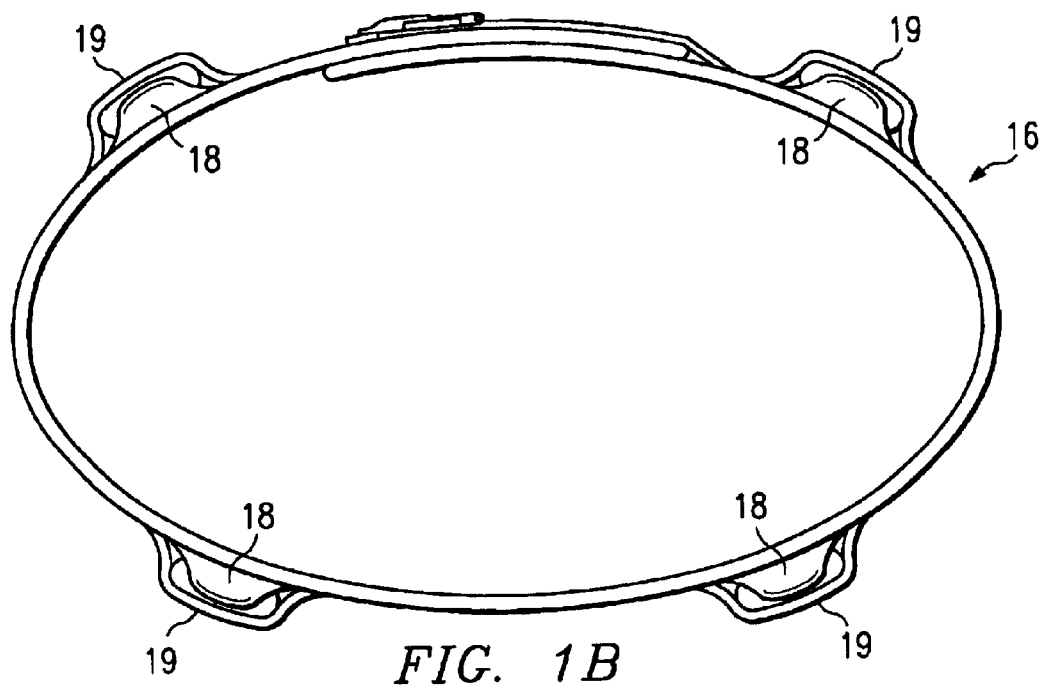
FIG. 1B is a cross-sectional drawing of a portion of the spinal traction device of FIG. 1B, showing example locations for lifting mechanisms associated with the traction device.
Figure 1C:
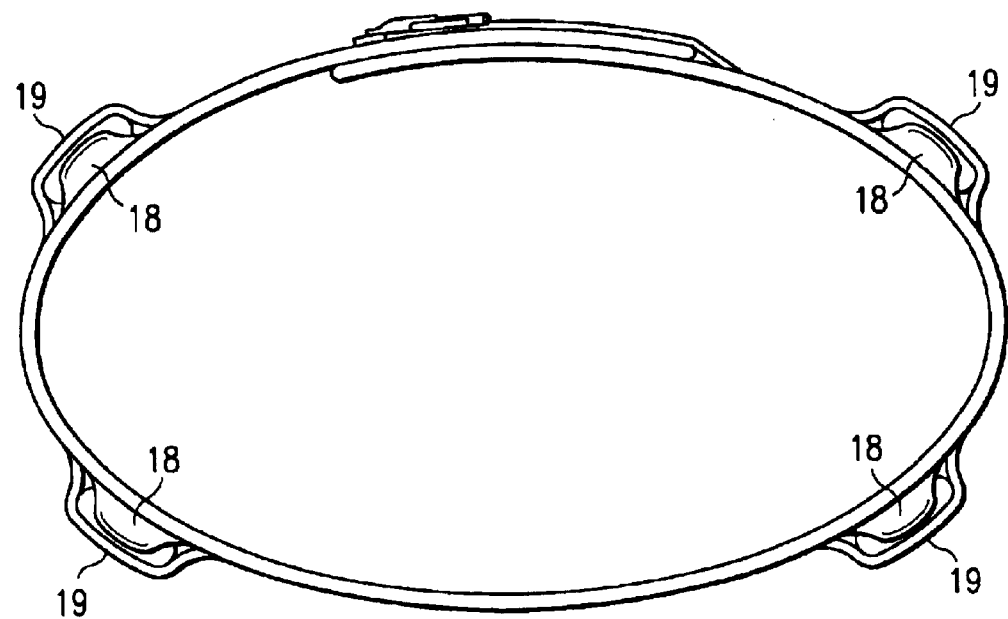
FIG. 1C is a cross-sectional drawing of a portion of the spinal traction device of FIG. 1B, showing example locations for an alternative embodiment of the invention.

FIGS. 1B and 1C are partial cross-sectional drawings through lines 1B—1B and 1C—1C, respectively, of FIG. 1A showing more clearly example locations for lifting mechanisms 18. FIG. 1B illustrates example locations for lifting mechanisms for normal spinal decompression use. As illustrated, four lifting mechanisms are used, with two in the general back region of user 12 and two located towards the front of user 12. This configuration allows application of a decompressive force to the spine yet allows user 12 to perform daily operations without undue hindrance. FIG. 1C illustrates a different configuration that also restricts motion of user 12 from side to side, in addition to placing the spine of user 12 into traction. This may be particularly useful for treating scoliosis. Scoliosis is a condition where the spine curves to one or two directions in the thoratic and/or lumbar region. The vertebrae of the spine are twisted or tilted, which causes the ribs to protrude to one side. By locating lifting mechanisms 18 towards the side of user 12, side-to-side motion by user 12 may be restricted and a straightening force may be applied to the spine to treat the spinal curvature effects of scoliosis. Although four lifting mechanisms are illustrated in both FIGS. 1B and 1C, any suitable number of lifting mechanisms may be used.

FIG. 2 is a schematic diagram of spinal traction device 10 showing additional details of lower support belt 16 and upper support belt 14. Upper support belt 14 is formed from a back belt 28 and a pair of front belts 30. Some portions of front belt 30 are not illustrated in FIG. 2 for clarity of illustration. Front belt 30 is formed with a plurality of holes 32 allowing selective adjustment of the size of upper belt 14. In conjunction, back belt 28 includes a plurality of slits 35 for engaging front belt 30 and a hole 34 for meshing with holes 32 in front belt 30. Front belt 30 and back belt 28 may be locked together through a rivet or other connector placed through a desired hole 32 and hole 34 on front belt 30 (not explicitly shown in FIG. 2). Surrounding front belts 30 and back belt 28 is an outer sleeve 31. Portions of outer sleeve 31 are cut away in FIG. 2. Outer sleeve 31 provides an attractive look to support belt 14 and also may provide cushioning comfort to user 12. Outer sleeve 31 may be formed from fabric or other suitable material and may be formed in a plurality of sections to facilitate selective access to back belt 28 and front belts 30 for adjustment.

Back belt 28 includes a strap 202 intermeshed between two plates 204. Back belt 28 is a generally rigid member in the direction of generalized support (up or down in this example) and is disposed within outer sleeve 31 of belt 14. As described in greater detail below, a force applied to upper back belt 28 from lifting mechanisms 18 is transferred to outer sleeve 31 and therefore the spine of user 12. Front belts 30 are also generally rigid in the direction of support and may be formed from plastic or other suitable material.

Top plate 202 and plates 204 are described in greater detail below with respect to FIGS. 6A and 6B; however particular portions associated with application of a decompressive force to belts 14 and 16 are described here. The plate 204 that is positioned to the exterior of strap 202 is formed with notches 36a. Notches 36a couple to portions of lifting mechanisms 18 and facilitate transferring of a decompressive force from lifting mechanisms 18 to upper belt 14. Plate 204 is generally rigid in the direction of support such that it may transfer a force resulting from lifting mechanisms "pushing" it. Plate 204 may be formed from any suitable material that allows transferring of force from lifting mechanisms 18 to a belt 14; however in one embodiment, plate 204 is formed from plastic. A notch 36a may have a substantially semi-circular shaped side curving in a direction generally away from lifting mechanism 18. Plate 204 is also be formed with slots 36b, each of which at least partially surrounds the corresponding notch 36a. Each slot 36b defines a portion of plate 204 that, because of slot 36b formed in elate 204, is enabled to rotate generally transverse to the surface of plate 204 that is adjacent the user's body (i.e. rotate generally toward and away from the user). As shown, slots 36b may be substantially semi-circular and may curve in a direction generally away from lifting mechanism 18. Ends of slots 36b may be enlarged into substantially circular openings.

Lower support belt 16 is similar to upper support belt 14. Lower support belt 16 includes a back belt 40 and a pair of front belts 42. Back belt 40 and front belts 42 are substantially similar to upper back belt 28 and front belt 30 and include a plate 44 and a strap 46; however, plate 44 is formed with notches 37a facing downward rather than upward to allow transference of force from lifting mechanisms 18 in a downward direction. A notch 37a may have a substantially semi-circular shaped side curving in a direction generally away from lifting mechanism 18, opposite the direction in which notch 36a curves. Similar to elate 204, plate 44 is also formed with slots 37b, each of which at least partially surrounds the corresponding notch 37a. Slot 37b defines a portion of plate 44 that, because of slot 37b formed in plate 44, is enabled to rotate generally transverse to the surface of plate 44 that is adjacent the user's body (i.e. rotate generally toward and away from the user). As shown, slots 37b may be substantially semi-circular and may curve in a direction generally away from plate 44. Ends of slots 37b may be enlarged into substantially circular openings.

Also shown more clearly in FIG. 2 is common strap 22. Common strap 22 connects to both upper belt 14 and lower belt 16, allowing common adjustment of spinal traction device 10 about the body of a user. In this example, hook and loop type fasteners 48, commonly known as Velcro™, are disposed on common strap 22 to secure strap 22 into place.

Figure 3:
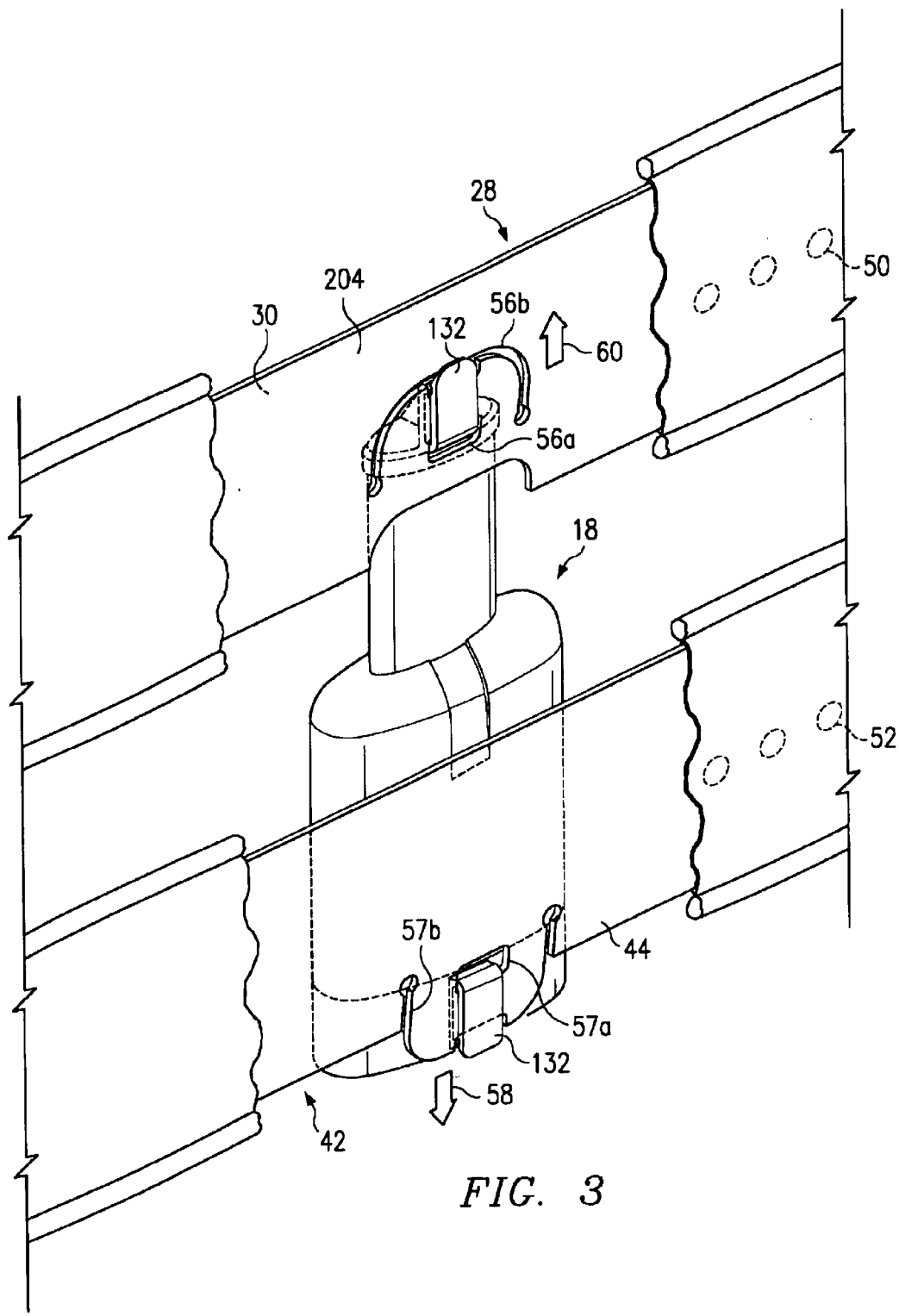
FIG. 3 is a schematic drawing with portions cut away showing in more detail one of the example lifting mechanisms of the spinal traction device of FIG. 1A.

One of holes 32 in front belt 30, denoted by reference numeral 50, and one of holes 32 in front belt 42, denoted by reference numeral 52, are also illustrated in FIG. 3.

FIG. 3 is a schematic diagram of portions of spinal traction device 10 with portions cut away showing additional details of coupling of lifting device 18 with upper belt 14 and lower belt 16. This figure may be oriented with respect to FIG. 2 by holes 50 and 52. As illustrated, front belt 30 includes a notch 56a, analogous to notches 36a, and front belt 42 includes a notch 57a, analogous to notches 37a. Lifting device 18 is coupled between belts 14 and 16 through notches 56a and 57a and clips 132, respectively, of lifting mechanisms 18. Access to notches 56a and 57a is provided through pouches 21 and 19, shown in FIG. 1A. A notch 56a, 57a may have a substantially semi-circular shaped side curving in a direction generally away from lifting mechanism 18, opposite the direction in which the other notch 57a, 56a curves. Front belt 30 also includes a slot 56b, analogous to slots 36b, and front belt 42 also includes a slot 57b, analogous to slots 37b, each of which at least partially surrounds the corresponding notch 56a or 57a, respectively. Slot 56b, 57b defines a portion of the corresponding front belt 30, 42 that, because of slot 56b, 57b formed in front belt 30, 42, is enabled to rotate generally transverse to the surface of front belt 30, 42 that is adjacent the user's body (i.e. to rotate generally toward and away from the user). As shown, slots 56b, 57b may be substantially semi-circular and may curve in a direction generally away from the corresponding front belt 30, 42. Ends of slots 56b, 57b may be enlarged into substantially circular openings. Additional details of lifting mechanism 18 are described in greater detail below in conjunction with FIGS. 4A through 4D.

In operation, in order to apply a decompressive force between upper belt 14 and lower belt 16, lifting device 18 is pressurized causing a downward force on the lower end of lifting device 18, as denoted by reference numeral 58 and an upward force on the upper end of lifting device 18, as denoted by reference numeral 60. This in turn generates forces in belt 30 and front belt 42 in opposite directions. Lifting mechanisms 18 may also be coupled between belts 14 and 16 at notches 36a and 37a in plates 204 and 44. Restriction of lifting mechanism 18 therefore results in applying a decompressive force to the spine of user 12 through belts 14 and 16. Additional details of examples of suitable lifting mechanisms 18 are described in greater detail below in conjunction with FIGS. 4A through 4D.

Figure 4A:
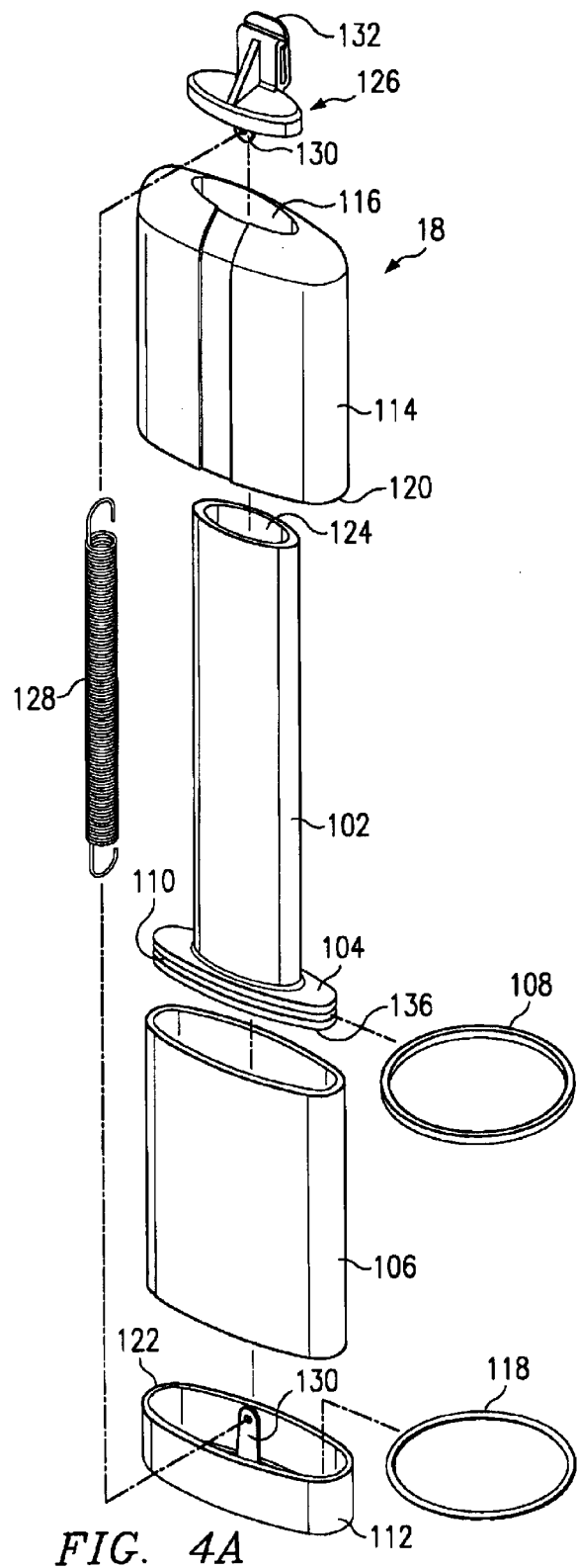
FIGS. 4A through 4D illustrate various views of an example lifting mechanism for use in a spinal traction device.
Figure 4B:
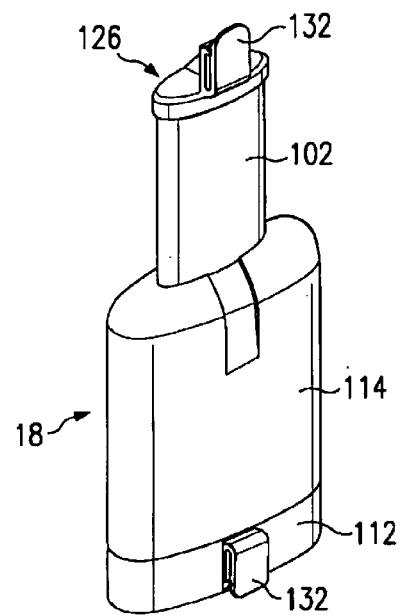
Figure 4C:
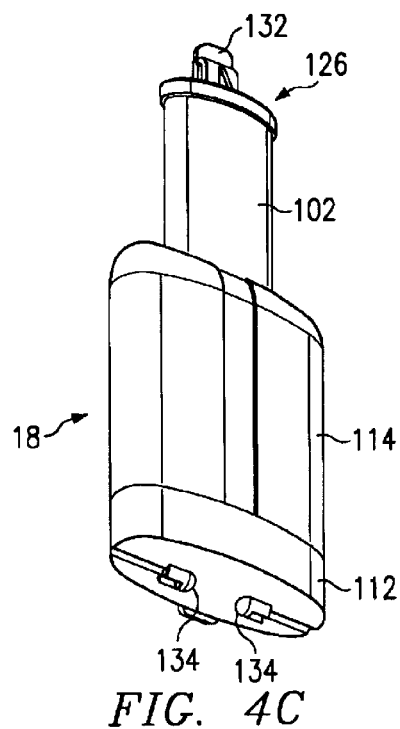
Figure 4D:
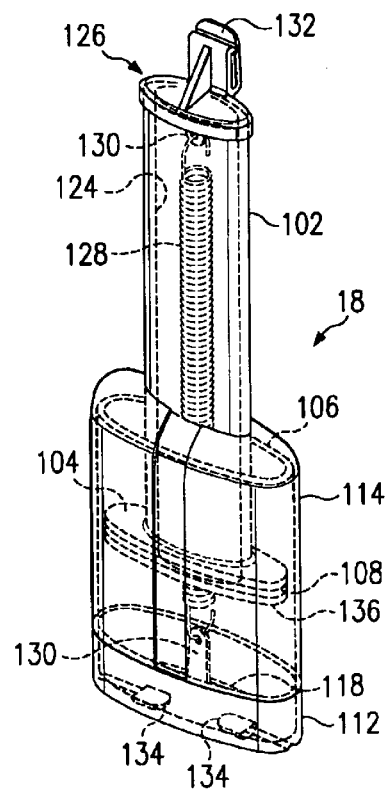

FIGS. 4A through 4D illustrate various views of an example lifting mechanism 18 for use in spinal or other traction device 10. FIG. 4A is an exploded view of lifting mechanism 18, FIGS. 4B and 4C are different isometric views of an assembled lifting mechanism 18, and FIG. 4D is a side view of lifting mechanism 18 illustrating internal components of lifting mechanism 18 using broken lines. Although lifting mechanisms are described, it should be understood that other types of support mechanisms may be used. For example, static support mechanisms may be used that do not extend (unlike lifting mechanisms 18), but that simply provide static support. As described above, one or more lifting mechanisms 18 may be coupled between support belts 14 and 16 or any other suitable supports (for example, between pins positioned in a user's bones on either side of a joint) and extended to provide separation of support belts 14 and 16, thus reducing the compressive forces applied to one or more of the vertebrae of user's spine (or any other suitable joint). As is illustrated, example lifting mechanism 18 has a substantially elliptical cross-section. The term "elliptical" is meant to include all noncircular ellipses, ovals, "egg" shapes, "bean" shapes, and any other similar shapes. When lifting mechanism 18 is positioned as a part of traction device 10, this substantially elliptical cross-section provides greater comfort to the user and has a lower profile against the user's body than would a similar lifting mechanism having a cylindrical cross-section. Furthermore, other shapes that conform to the user's body may also be used. However, as described below, the use of such substantially elliptical or other non-circular cross-sections present problems that are not associated with a cylindrical cross-section.

Lifting mechanism 18 includes a piston having a piston rod 102 and a flange 104 that is inserted into a sleeve 106. In the illustrated embodiment, piston rod 102, flange 104, and sleeve 106 each have a substantially elliptical cross-section. However, any other appropriate shape may be used for one or more of these components. For example, flange 104 and sleeve 106 may have substantially elliptical cross-sections and piston rod 102 may have a circular or other appropriate cross-section. Flange 104 is configured such that it conforms to the inside of sleeve 106 and may slide inside sleeve 106. A piston ring 108 may be positioned around the perimeter of flange 104 to form a seal between flange 104 and sleeve 106. A groove 110 may be formed around the perimeter of flange 104 to provide a seating for piston ring 108. Piston ring 108 may have a rectangular cross-section, a circular cross-section, or any other appropriate type of cross-section. Furthermore, piston ring 108 may be fabricated from rubber or any other appropriate material.

Since sleeve 106 has a non-circular cross-section, if the interior of sleeve 106 is pressurized to effect the movement of piston rod 102 (as described below), stresses will be developed in sleeve 106 and give sleeve 106 the tendency to deform into a cylindrical shape. This is undesirable since it may induce leakage between sleeve 106 and piston ring 108. Therefore, sleeve 106 may be fabricated from a metal, such as aluminum, or another appropriate material to withstand these stresses and prevent such deformation. In the example embodiment, sleeve 106 has openings at either end and thus does not form an airtight chamber into which air or any other appropriate fluid may be inserted to move piston rod 102. Therefore, to form an airtight chamber, a housing is formed around sleeve 106. The housing includes a housing bottom 112 which fits over one end of sleeve 106 and a housing top 114 which fits over the other end of sleeve 106 and contacts housing bottom 112. Housing top 114 also provides an opening 116 through which piston rod 102 may be extended. A housing ring 118 may be inserted into housing bottom 112 to provide a seal between sleeve 106 and housing bottom 112 to prevent or reduce the leakage of air or other fluids from sleeve 106. A lower edge 120 of housing top 114 may be sonically welded to a upper edge 122 of housing bottom 112, although housing bottom 112 and housing top 114 may be coupled in any other appropriate manner to form a substantially airtight enclosure. Housing bottom 112 and housing top 114 may be fabricated from plastic or any other suitable material. Furthermore, housing top 114 may be eliminated in certain embodiments and sleeve 106 may have a partially enclosed first end and be bonded with housing bottom 112 at a second end. However, housing top 114 may be used when bonding between sleeve 106 and housing bottom 112 is infeasible due to the use of differing materials to fabricate sleeve 106 and housing bottom 112.

In particular embodiments, piston rod 102 may be hollow such that a cavity 124 extends from one end of piston rod 102 to the other. Cavity 124 extends through flange 104 such that air or another fluid in sleeve 106 may travel through piston rod 102 in cavity 124. Therefore, a piston rod top 126 is coupled to the end of piston rod 102 opposite flange 104 to prevent this air or other fluid from escaping from sleeve 106 through piston rod 102. Piston rod top 126 may be sonically welded to piston rod 102 or coupled to piston rod 102 using any other suitable technique. As with piston rod 102, piston rod top 126 may be fabricated from plastic or any other appropriate material. Cavity 124 is provided in particular embodiments so that a spring 128 or other appropriate elastic member may be used to connect housing bottom 112 and piston rod top 126. Spring 128 is used to provide a force to retract piston rod 102 into sleeve 106 when a sufficient air or other fluid pressure does not exist in sleeve 106 to counteract the retraction force generated by spring 128, such as when traction device 10 is not in use. Housing bottom 112 and piston rod top 126 may each include a hook point 130 which may be used to attach spring 128 to housing bottom 112 and piston rod top 126. Alternatively, any other appropriate attachment points located in any other suitable positions may be used. Housing bottom 112 and piston rod top 126 may also include clips 132 for coupling lifting mechanism 18 to support belts 14 and 16, as described above.

As shown in FIG. 4C, housing bottom 112 also includes one or more inlets 134 through which air or any other appropriate fluid may be pumped into and released from sleeve 106. For example, inlets 134 may be configured such that a hose from an associated pump may be coupled to inlets 134. Using such a pump, air or another fluid may be pumped into sleeve 106 until a sufficient amount of pressure is exerted against a bottom face 136 of flange 104 (shown in FIG. 4A), and against piston rod top 126 if piston rod 102 is hollow to cause flange 104 to move away from housing bottom 112 and thus for piston rod 102 to extend out from housing top 114. Air or any other appropriate fluid may be pumped into sleeve 106 through inlets 134 until piston rod 102 is in an appropriate position. As described above, multiple lifting mechanisms 18 may be coupled between support belts 14 and 16, and the piston rod 102 of each lifting mechanism 18 may be extended such that appropriate spacing is maintained between support belts 14 and 16 and an appropriate force is applied to place the user's spine or other joint in traction. Once this appropriate position and force are reached, the pressure against flange 104 (and piston rod top 126, if appropriate) are maintained to provide support to the user and reduce compressive forces on the user's spine or other joint.

Figure 5:
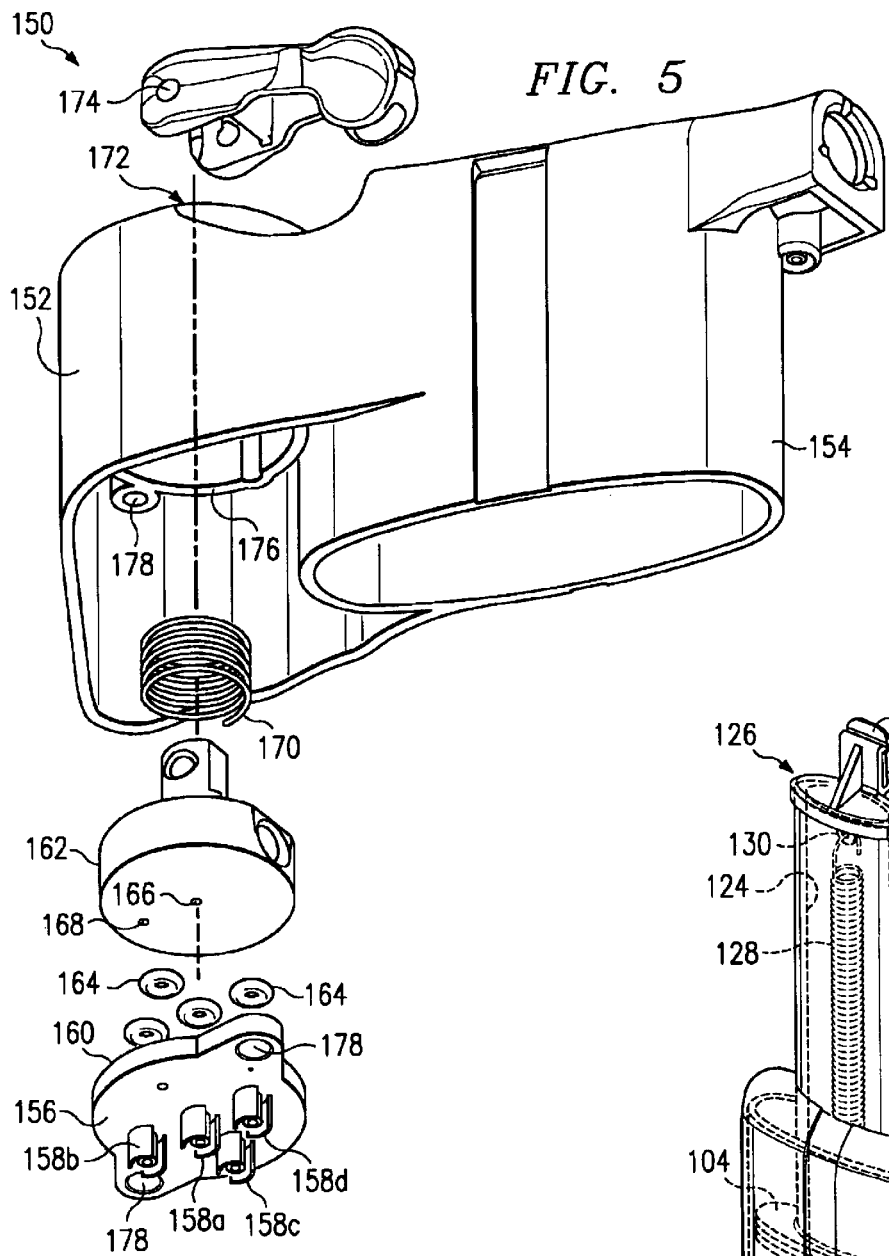
FIG. 5 illustrates an example valve assembly of a spinal traction device.

FIG. 5 illustrates an exemplary valve assembly 150 of traction device 10. Valve assembly 150 may be used to connect multiple lifting mechanism 18 to a pump used to pump air or any other appropriate fluid into lifting mechanism 18. For example the multiple lifting mechanisms 18 of traction device 10 may be connected to a pump in series or in parallel by appropriately connecting inlets 134. For example, a hose may be coupled between valve assembly 150 (as described below) and a first inlet 134 of a first lifting mechanism 18. Another hose may be coupled between a second inlet 134 of the first lifting mechanism 18 (as illustrated in FIG. 4C, each lifting mechanism 18 may have multiple inlets 134) and a first inlet 134 of a second lifting mechanism 18. Such a pattern may be continued until each lifting mechanism 18 is either connected to another lifting mechanism 18 or to valve assembly 150. A pump may then be coupled to valve assembly 150 to pump air or another fluid into the various lifting mechanisms 18, as described below. Alternatively, each lifting mechanism 18 may be individually coupled to valve assembly 150 or subsets of the lifting mechanism 18 may be coupled in series and then coupled to valve assembly 150. For example, two front lifting mechanisms 18 may be coupled in series and two back lifting mechanism 18 may be coupled in series separate from the front lifting mechanisms 18.

Valve assembly 150 provides a point at which the various lifting mechanisms 18, no matter how interconnected, may be coupled to a pump. In the illustrated embodiment, valve assembly 150 is formed integrally with one of the lifting mechanisms 18 of traction device 10. For example, a housing 152 of valve assembly 150 may be formed integrally with a housing 154 of the associated lifting device (housing 154 may be used in place of housing 114, described above). However, valve assembly 150 may also be fabricated as a stand-alone device that may be associated with traction device 10 in any appropriate manner.

Valve assembly 150 includes a valve plate 156 that includes a number of couplers 158 to which hoses may be coupled. For example, a hose from a pump may be coupled to coupler 158a, which is located in the center of plate 156. Similarly, hoses leading to one or more lifting mechanisms 18 or other devices to which air or another fluid is to be supplied (for example, a lumbar pillow associated with lower support belt 14) may be coupled to couplers 158b–158d. Any appropriate number of couplers 158 may be included in valve assembly 150. Plate 156 further includes a series of holes, with each hole extending from a coupler 158 through, plate 156 to an upper surface 160 of plate 156. Therefore, air or another fluid may travel from upper surface 160 of plate 156 through each of these holes to a hose attached to the respective coupler 158, and vice versa. When assembled, plate 156 is positioned concentric to and proximate a plunger 162 and is separated from plunger 162 by a number of O-rings 164 or other appropriate seals. Each O-ring 164 is positioned around a respective hole in plate 156. Plunger 162 includes a center hole 166 that extends through plunger 162 and aligns with a center hole in plate 156 (extending from coupler 158a). Plunger 162 also includes a side hole 168 that extends through plunger 162 and is located the same distance from the center of plunger 162 as the distance the holes associated with couplers 158b–158d are located from the center of plate 156.

A spring 170 is positioned between plunger 162 and an upper inner surface 172 of housing 152. Spring 172 applies a force to plunger 162 that causes plunger to be pressed against and form a seal with plate 156 (with the aid of O-rings 164). An airtight enclosure is formed in the top portion of housing 152 above plunger 162 by coupling plate 156 to housing 152, for example, with one or more appropriate fasteners. Plunger 162 is coupled to a valve lever 174, which is located outside of housing 152. Lever 174 may be used to rotate plunger 162 or to raise plunger 162 so as to break the seal between plunger 162 and plate 156. Furthermore, an airtight enclosure is formed between plate 156 and plunger 172 by fastening plate 156 against a lip 176 of housing 152. For example, holes 178 may be used to fasten plate 156 against lip 176 using screws or other appropriate fasteners.

When plunger 162 is in contact with plate 156, air or another fluid from a pump coupled to coupler 158a may pass through plate 156 (in the hole associated with coupler 158a) and then through hole 166 of plunger 162 into the airtight enclosure above plunger 162. The air or other fluid then travels back down through hole 168 of plunger 162. Where the air travels after this depends on where hole 168 is positioned. Lever 174 may be used to rotate plunger 162 such that hole 168 may be aligned with a hole in plate 156 corresponding to coupler 158b, 158c, or 158d. When hole 168 is aligned with one of these holes in plate 156, the air may then travel through the hole in plate 156 to the hose attached to the corresponding coupler 158b, 158c, or 158d. The air then travels through the corresponding hose to the one or more lifting mechanisms 18 or other pressurized devices attached to the hose.

This process may be repeated for the devices coupled to each coupler 158b–158d by rotating plunger 162 so that hole 168 is aligned with the appropriate hole in plate 156. A check valve may be included in plunger 162 in-line with hole 166 to prevent air or another fluid from the various attached pressurized devices from returning through hole 166 and thus escaping through the hole in plate 156 corresponding with coupler 158a, for example, when no pump is coupled to coupler 158a. When a user desires to release the air or another fluid from the various attached pressurized devices, the user may use lever 174 to lift plunger 162 off of plate 156. When this happens, the air or other fluid from each of the devices passes from the various hoses coupled to couplers 158b–158d through plate 156 and then back through plate 156 through the hole associated with coupler 158a (if a pump is not coupled to coupler 158a) or through another suitable outlet.

FIG. 6A illustrates an example back belt 28 included in a support belt 14 of traction device 10, viewed from the rear. Back belt 28 may be coupled to front belts 31 of support belt 14 using holes 32 and 34 and an associated connector, as illustrated in FIG. 2, with strap 202 being internal to plate 204 (closer to the user's body) to accommodate lifting mechanisms 18. However, it should be noted that support belt 14 may include a single belt that includes the features of both back belt 28 and front belts 31. Back belt 28 includes a strap 202 and a plate 204. FIG. 6B illustrates strap 202 without plate 204 to more clearly illustrate strap 202. As described above, plate 204 includes notches 36 that are used to connect lifting mechanisms 18 to support belts 14 and 16. For example, clips 132 of a lifting mechanism 18 may be inserted into notches 36 to attach the lifting mechanism 18 to support belt 14. In the example embodiment, strap 202 is coupled to plate 204 at two pivots 206. Pivots 206, along with a canting mechanism 208 incorporated in strap 202, allow strap 202 to move in relation to plate 204 (and thus in relation to lifting mechanisms 18) to assist in fitting support belts 14 and 16 to the user's body, as described below. Any appropriate component may be used to couple strap 202 and plate 204 at pivots 206 so as to allow strap 202 and plate 204 to rotate relative to one another at pivots 206.

Strap 202 includes a first portion 210a and a second portion 210b that are coupled using canting mechanism 208. In one embodiment, canting mechanism 208 includes two hinges 212a and 212b. Plate 204 and canting mechanism 208 are typically positioned on the user's back near the spine when traction device 10 is worn by the user. Portions 210 typically extend from the user's back and around the user's sides to the user's front. When worn in such a manner, pivots 206 and hinges 212 of canting mechanism 208 allow portions 210 to conform to the contours of the user's body, and particularly to the areas of the thorax and the pelvis. Therefore, canting mechanism 208 may be used to more closely fit support belts 14 and 16 to users having a variety of different sizes and shapes, while maintaining substantial symmetry and more effective treatment.

As is illustrated in FIGS. 6A and 6B, portions 210 and canting mechanism 208 may be integrally formed. For example, portions 210 and canting mechanism 208 may be formed from a single piece of plastic and hinges 212 may be formed by molding or cutting this piece of plastic into the desired shape. Alternatively, any other suitable method of fabricating these components from any appropriate material may be used. Hinges 212a and 212b may be formed by forming or cutting slots 214a and 214b, respectively, in strap 202. The term "slots" is meant to include both slits and wedges formed in strap 202. If slits are formed, the slits are pulled open to create wedges when strap 202 is coupled to plate 204. As illustrated in FIG. 6B, slot 214a associated with hinge 212a begins at a first edge 216 of strap 102 and extends almost to a second edge 218 of strap 202. The remaining material of strap 202 between the end of slot 214a and second edge 218 of strap 202 forms hinge 212a. Furthermore, a circular or other cut-out may be formed at the end of slot 214a near second edge 218 to aid in the opening of slot 214 and to reduce the resultant stresses on hinge 212a. Slot 214b is formed in a similar manner except that slot 214b begins at second edge 218 of strap 202 and extends almost to first edge 216 of strap 202. Hinge 212b is located proximate to first edge 216 and provides a different point of rotation than hinge 212a. Therefore, hinges 212a and 212b may be collectively referred to as a polycentric hinge.

If slots 214 are formed as wedges in strap 202, the width of wedges 214 and the angle at which wedges 214 are formed determines, at least in part, the range of movement of portions 210. For example, the greater the size of wedges 214, the more range of movement that will be allowed. If slots 214 are formed as slits, the slits are opened to form wedges having an appropriate size. Furthermore, the positioning of hinges 212 ensures that the movement of portions 210 is complementary. For example, if an end 220a of portion 210a moves up, then an end 220b of portion 210b will move up a substantially equal amount. This is because the upward movement of end 220a will cause slot 214a to close about hinge 212a, and this closure of hinge 214a will in turn cause slot 214b to open about hinge 212b (due to forces applied and the positioning of pivots 206). This closure of hinge 214b will in turn cause an upward movement of end 220b. Therefore, the design of canting mechanism 208 allows for the movement of portions 210a and 210b of strap 202 and synchronizes this movement.

Referring again to FIG. 6A, depending upon which part of the user's body that back belt 200 is to be positioned around, one or more limitors 222 may be used to limit the movement of portions 210 in a certain direction. For example, if back belt 200 is to be positioned around the user's hips with first edge 216 of strap 202 nearest to the user's legs, then limitors 222 may be positioned as illustrated to allow portions 210 to move upward to accommodate the user's hips, but not allow downward movement of portions 210 past a certain point. Limitor slots 224 may be formed in strap 202 and may be configured and positioned such that when portions 210 are moved downward, limitor slots 224 engage with limitors 222 on plate 204 and prevent further downward movement of portions 210 with respect to plate 204. In this case, limitors 222 may be peg-like extensions from plate 204 on the side of plate 204 to which strap 202 is attached. Although limiting the downward movement of portions 210 is described, it should be understood that limitors 222 and limitor slots 224 may be positioned in other embodiments so as to limit the upward and/or downward movement of portions 210.

Figure 7:
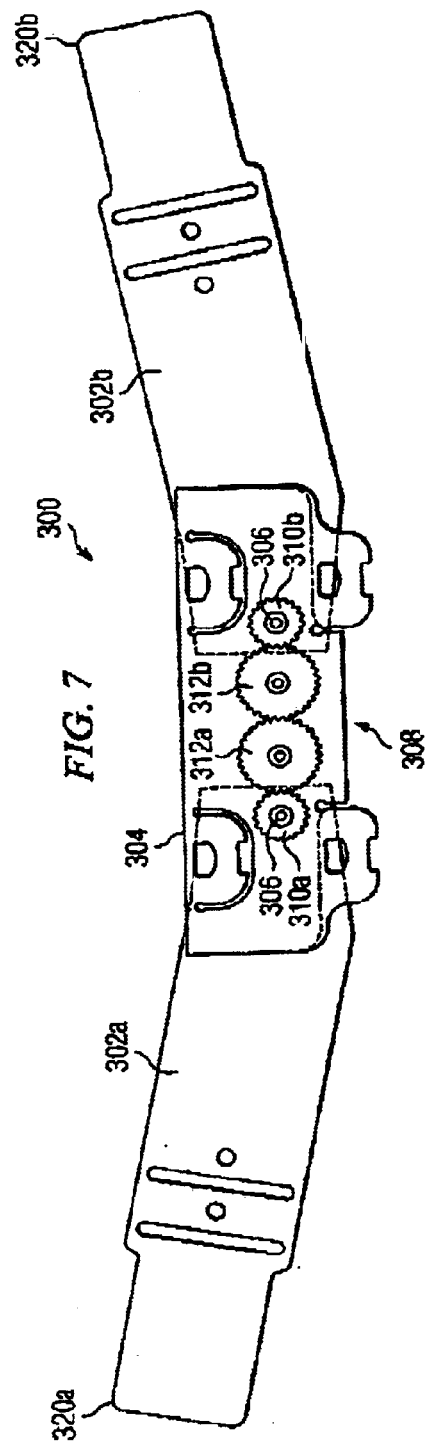
FIG. 7 illustrates another example back belt included in a support belt of a spinal traction device.

FIG. 7 illustrates another example back belt 300 included in a support belt 14 of traction device 10. Back belt 300 includes a strap having two separate portions 302a and 302b and also includes a plate 304 coupling portions 302a and 302b. As with plate 204, lifting mechanisms 18 are coupled to plate 304. Portions 302 are coupled to plate 304 at pivots 306, such that portions 302 may move independently of plate 304. Back belt 300 also includes a canting mechanism 308. However, unlike canting mechanism 208 of FIGS. 6A and 6B, canting mechanism 308 is implemented using a series of gears. In one embodiment, these gears include strap gears 310a and 310b which are rotatably coupled to portions 302a and 302b, respectively, and plate gears 312a and 312b which are rotatably coupled to plate 304. Gears 310 and 312 may be fabricated from plastic, metal, or any other appropriate material.

Gears 310 and 312 may be coupled to one another in the following manner. Gear 310a meshes with gear 312a, gear 312a meshes with gear 312b, and gear 312b meshes with gear 310b. Therefore, if gear 310a is rotated, this rotation also causes gears 312a, 312b, and 310b to rotate. Gears 310a and 310b are coupled to portions 302a and 302b, respectively, such that when a portion 302 rotates about its respective pivots 306, the respective strap gear 310 associated with the portion 302 also rotates about the pivot 306. Since gears 310 are coupled through gears 312, if one portion 302 is moved upward or downward, the other portion 302 moves substantially the same distance in the same direction.

For example, if an end 320a of portion 302a is raised (for example, to fit over a user's hip), then this motion will cause gear 310a to rotate in a clockwise direction and the degree of this rotation will be relative to the distance that end 320a raised. The clockwise rotation of gear 310a will in turn cause a counter-clockwise rotation of gear 312a, and this rotation of gear 312a will cause a clockwise rotation of gear 312b. Finally, the clockwise rotation of gear 312b will cause a counter-clockwise rotation of gear 310b, which in torn will chase an end 320b of portion 302b to move substantially the same distance upward as end 320a was moved. Furthermore, although not illustrated in FIG. 7, back belt 300 may have limitors and limitor slots (as with back belt 200) to limit the movement of straps 302a and 302b in one or more directions, as described with reference to FIGS. 6A and 6B above. Moreover, although two example canting mechanisms for facilitating the manipulation of a support belt 14 to fit the contours of a user's body while maintaining substantial symmetry are described, any other appropriate mechanisms may be used and are included within the scope of the present invention.

Figure 8:
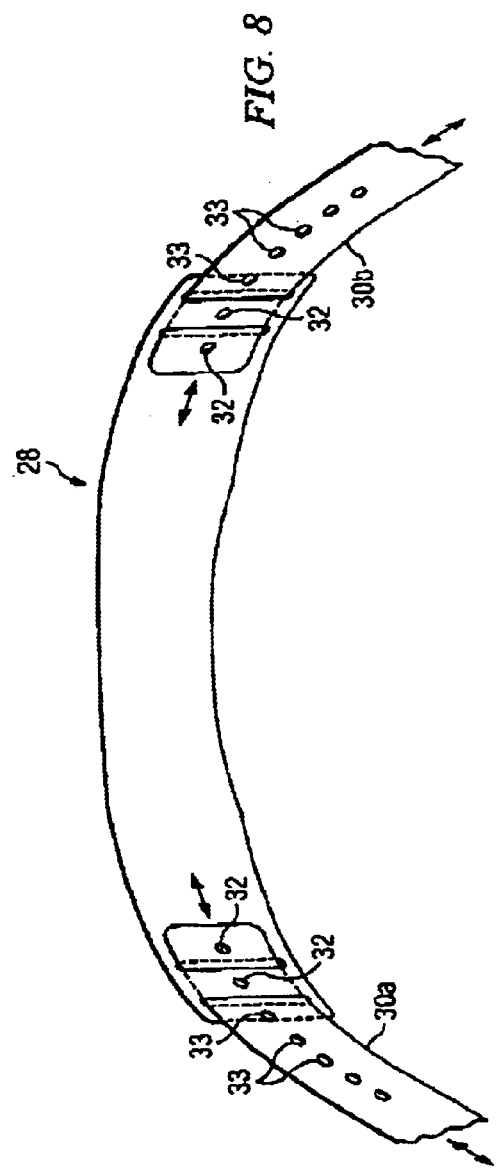
FIG. 8 is a schematic diagram illustrating a portion of the spinal traction device of FIGS. 1A through 1D, showing portions of one of the belts.

FIG. 8 is a schematic diagram illustrating portions of upper support belt 14 of traction device 10 of FIGS. 1A through 1C, illustrating the movable relationship between front belts 30a, 30b and back belt 28. Front belts 30a and 30b may be adjusted relative to back belt 28 to appropriately fit a user. Adjustment of front belts 30a and 30b with respect to back belt 28 is referred to as a macro adjustment because additional adjustments may be made through latches 24 and 26 and common strap 22. Lower belt 16 may be adjusted in a similar manner.

In the illustrated embodiment, back belt 28 is formed with a pair of holes 32 for intermeshing and coupling with one of holes 33 formed in front belts 30a and 30b. Use of holes 32 and 33 may sometimes allow suitable adjustments of front portions 30a and 30b such that a user may pull on both 30a and 30b and increase the length equally from both sides; however it is often difficult to ensure that front belts 30a and 30b have been lengthened by the same number of holes 33. In addition, in embodiments that do not utilize holes 32 and 33, such as embodiments that utilize clamps or other suitable connecting mechanisms for joining front belts 30a and 30b to back belt 28, it is often difficult to lengthen belt 14 equally from both sides. If upper belt 14 is not lengthened equally from both sides, this may skew the position of lifting mechanisms 18 to an undesired position. Therefore, an adjustment mechanism is provided that facilitates lengthening belt 14 to a suitable size but maintains the appropriate orientation of the associated lift mechanisms 18. An example embodiment of such a mechanism is described below in conjunction with FIGS. 9A through 9C.

Figure 9A:
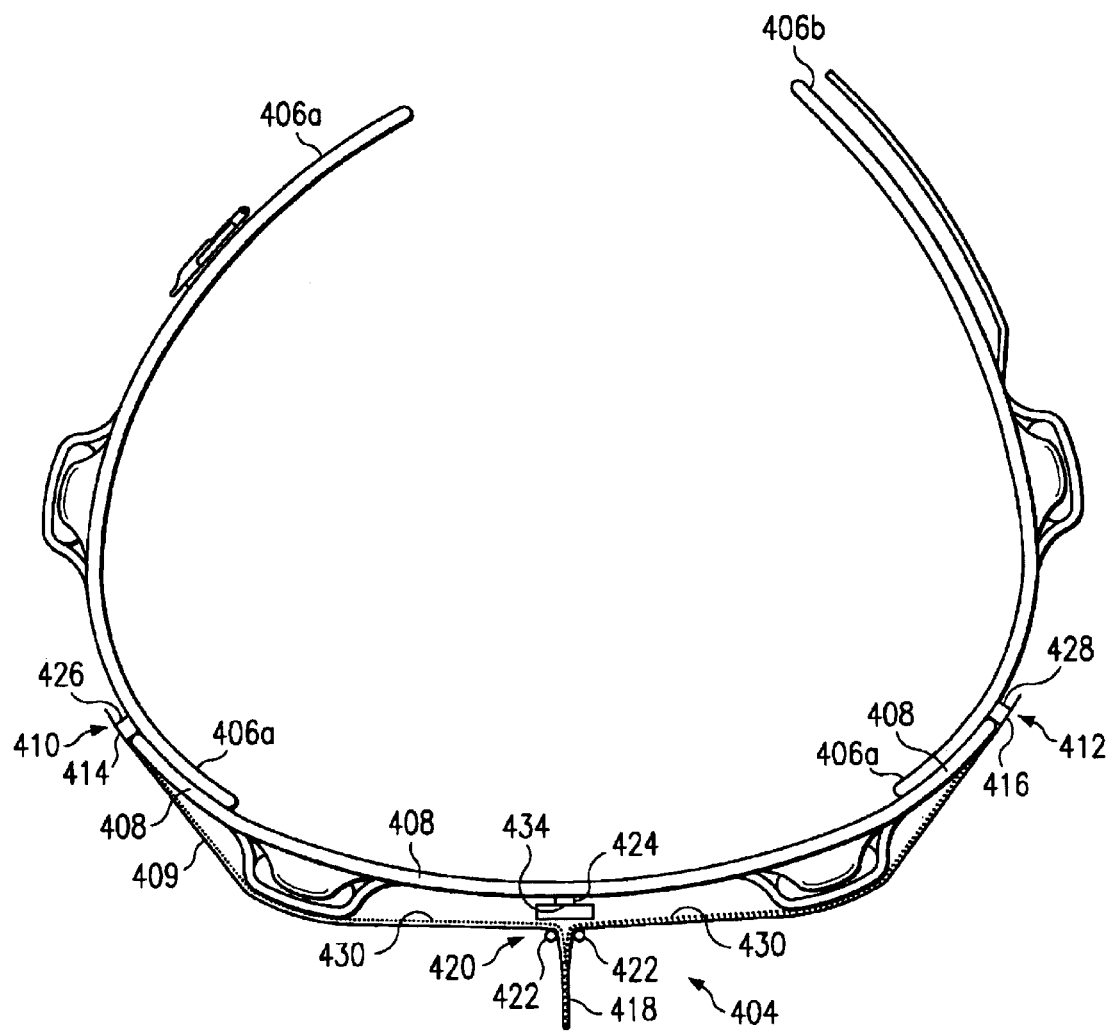
FIG. 9A is a top view of an example support belt and length adjustment mechanism combination in a first, unadjusted position.

FIG. 9A is a top view of a belt 402 in combination with an adjustment mechanism 404 according to the teachings of the invention. Belt 402 may be similar to upper belt 14 or lower belt 16 and includes front portions 406a and 406b that may be connected to a back portion 408. Belt 402 is lengthened by pulling together front portions 406a and 406b thus pulling the front portions away from back portion 408. As described above, it is often difficult to pull equally on front portion 406a and 406b to maintain the desired orientation of belt 402 about the body of a user. When utilizing lift mechanisms 18, this disorientation could result in improper fitting of the belt and improper forces being applied to the user. Therefore, an adjustment mechanism 404 is provided. Adjustment mechanism 404 includes a strap 409 having ends 410 and 412 coupled to front portions 406a and 406b, respectively. As used herein, "ends" refers generally to opposite portions of strap 409; however, ends 410 and 412 are not required to be the termination of strap 409. Ends 410 and 412 may couple to front portions 406a and 406b, respectively through any suitable manner, such as snap combinations 414, 426 and 416, 428. Adjustment mechanism 408 also includes a clamp 420 coupled to back belt 408 through snap combination 424, 434. Clamp 420 includes rollers or bars 422 that guide strap 409 along back belt 408. A hook and loop material, commonly known as Velcro, is formed on strap 409 between rollers 422, as denoted by reference numeral 418. Strap 409 may also include this hook and loop material on other portions of it. Operation of adjustment mechanism 408 is described with reference to FIG. 9B.

Figure 9B:
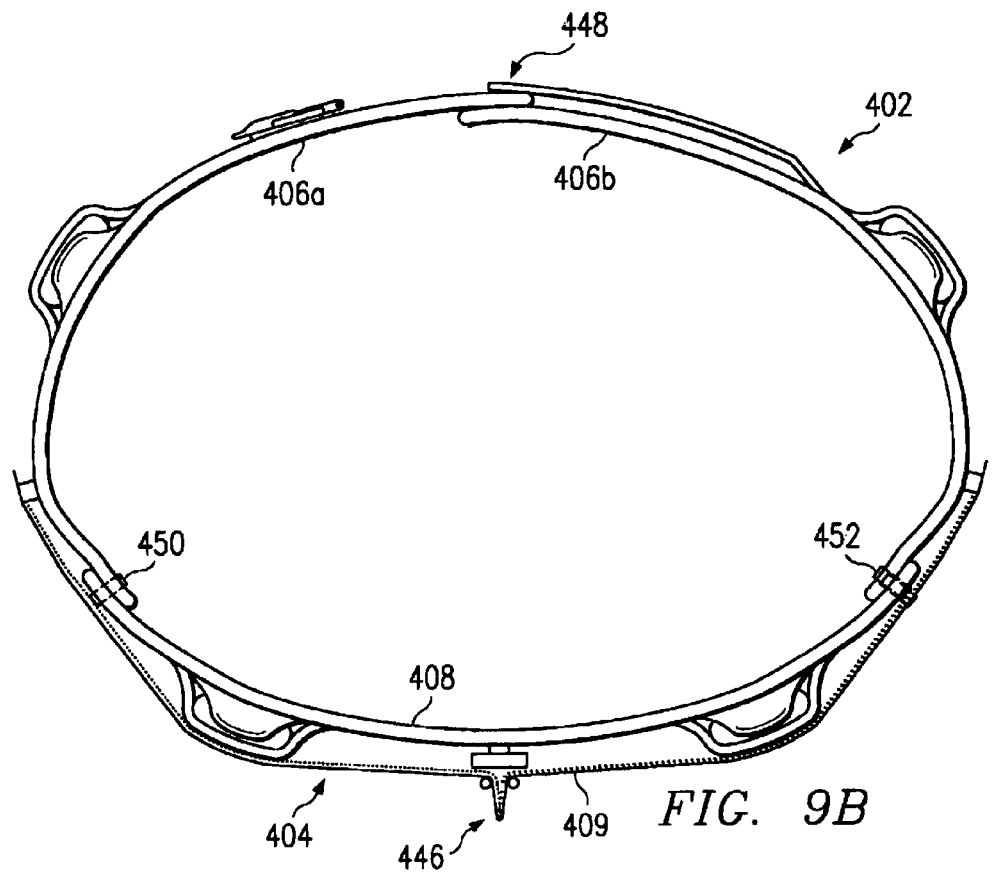
FIG. 9B is a top view of the combination of FIG. 9B in a adjusted position.

FIG. 9B is a top view of the belt and adjustment mechanism 408 and belt 402 of FIG. 9A showing belt 402 in an adjusted position. As shown, front portions 406a and 406b have been pulled together, as denoted by reference numeral 448, thus increasing the length of belt 402. Pulling front portions 406a and 406b together necessarily pulls strap 409 and hook and loop portion 418 along with it. In doing so, hook and loop portion 418 detaches from each other, which causes strap 409 to be pulled equally from both the side of 406a and the side of 406b. This ensures that the resulting configuration of belt 402 maintains the proper orientation for lift mechanisms such as those described above. Front belts 406a, 406b may then be secured to back belt 408 by rivets or other suitable connectors 450 and 452.

Figure 9C:
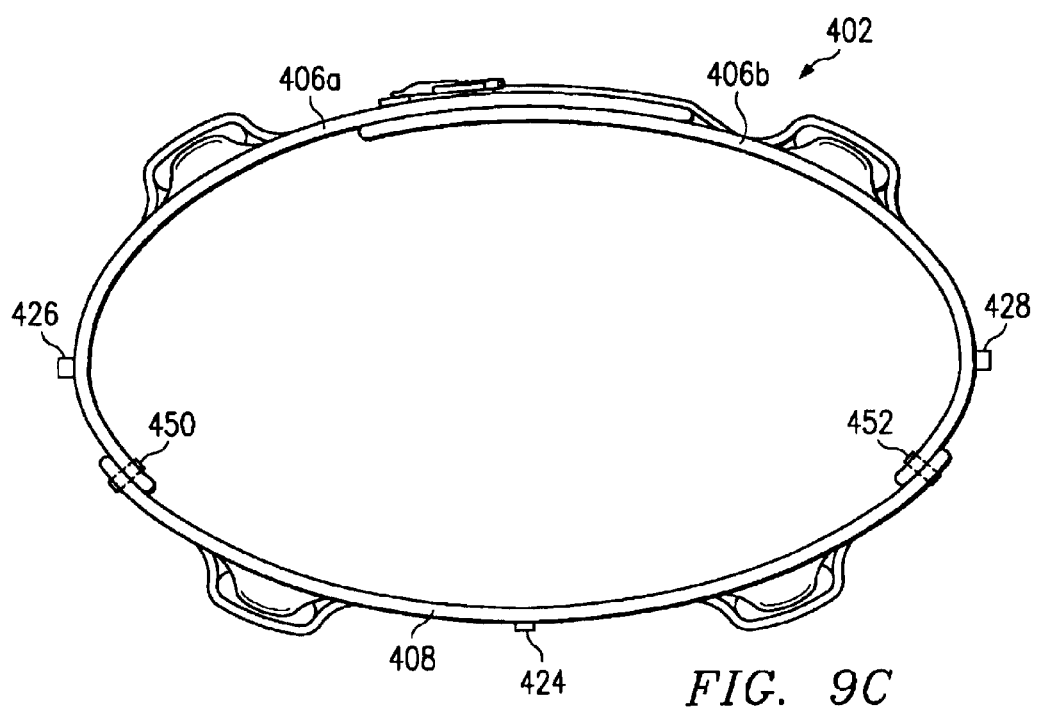
FIG. 9C is a top view of a support belt after removal of the adjustment mechanism of FIGS. 9A and 9B.

FIG. 9C is a top view of the belt 402 shown in FIGS. 9A and 9B after detachment of adjustment mechanism 404. After belt 402 is suitably adjusted, as described in FIG. 9B, adjustment mechanism 404 may be detached at ends 410 and 412 as well as clamp 420, leaving the device as shown in FIG. 9C. Thus a macro adjustment for belt 402 may be effected that ensures proper orientation of associated lifting mechanisms, while fine tuning of the fit or belt may be accomplished through common strap 22 and locking devices 20.

Although the present invention has been described with several embodiments, numerous changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:

1. An ambulatory traction device, comprising:
   a first support configured to be positioned on a user's body;
   a second support configured to be positioned on the users body such that a portion of the user's body is positioned between the first and second supports; and
   one or more lifting mechanisms each coupling the supports and operable to apply a decompressive force to the portion of the user's body when the supports are positioned on the, user's body, each lifting mechanism comprising:
   a sleeve having a non-circular cross-section and operable to contain a fluid; and
   a piston configured to move within the sleeve in response to an increase in fluid pressure within the sleeve.

2. The device of claim 1, wherein the device is an ambulatory spinal traction device, the supports are support belts, and the portion of the user's body comprises at least a portion of the user's spine.

3. The device of claim 1, wherein the piston comprises a non-circular flange adapted to seal against the sleeve and the lifting mechanism further comprises a housing conformed to the sleeve, the housing preventing the flange from exiting the sleeve, the sleeve, housing, and flange collectively forming a substantially fluid-tight enclosure.

4. The device of claim 3, wherein the sleeve is fabricated from a non-plastic material and the housing is fabricated from a plastic material.

5. The device of claim 3, wherein: the piston comprises a piston rod and a flange adapted to seal against the sleeve; and the housing defines an opening through which the piston rod may move, but through which the flange may not move.

6. The device of claim 3, wherein:
   the housing has an interior height between a first location substantially near a bottom of the housing and a second location substantially near a top of the housing; and
   the flange of the piston is operable to travel over the entire interior height depending on the fluid pressure within the sleeve, the flange of the piston being located at the first location substantially near the bottom of the housing when the fluid pressure within the sleeve is at its minimum, the flange of the piston being located at the second location substantially near the top of the housing when the fluid pressure within the sleeve is at its maximum.

7. The device of claim 3, wherein the housing comprises one or more inlets positioned such that a fluid may be pumped through the inlets into the substantially fluid-tight enclosure.

8. The device of claim 1, wherein the piston comprises a flange adapted to seal against the sleeve and the lifting mechanism further comprises a piston ring configured to surround a perimeter of the flange to assist in forming a substantially fluid-tight seal between the flange and the sleeve.

9. The device of claim 1, wherein the piston defines a cavity fluidly coupled to an interior of the sleeve and extending through the piston.

10. The device of claim 9, wherein the lifting mechanism further comprises an elastic member positioned in the cavity and coupled to the piston, the elastic member operable to refract the piston in response to a decrease in fluid pressure within the sleeve.

11. The device of claim 10, wherein the elastic member comprises a spring.

12. The device of claim 10:
wherein the housing has an interior height between a first location substantially near a bottom of the housing and a second location substantially near a top of the housing; and
wherein, as a result of the elastic member positioned within the cavity of the piston, the piston is operable to travel over the entire interior height depending on the fluid pressure within the sleeve, the piston being located at the first location substantially near the bottom of the housing when the fluid pressure within the sleeve is at its minimum, the piston being located at the second location substantially near the top of the housing when the fluid pressure within the sleeve is at its maximum.

13. The device of claim 10, wherein:
the housing has a height;
the piston has a maximum amount of extension from the housing; and
the lifting mechanism has a maximum height that is substantially equivalent to the height of the housing plus the maximum amount of extension of the piston.

14. A lifting mechanism for use with an ambulatory traction device, the lifting mechanism configured to be coupled between two supports of the traction device such that a portion of a user's body is positioned between the supports, the lifting mechanism operable to apply a decompressive force to the portion of the user's body when the supports are positioned on the user's body, the lifting mechanism comprising:
a sleeve having a non-circular cross-section and operable to contain a fluid; and
a piston configured to move within the sleeve in response to an increase in fluid pressure within the sleeve.

15. The lifting mechanism of claim 14, wherein the ambulatory traction device is an ambulatory spinal traction device, the supports are support belts, and the portion of the user's body comprises at least a portion of the user's spine.

16. The lifting mechanism of claim 14, wherein the piston comprises a non-circular flange adapted to seal against the sleeve and the lifting mechanism further comprises a housing conformed to the sleeve, the housing preventing the flange from exiting the sleeve, the sleeve, housing, and flange collectively forming a substantially fluid-tight enclosure.

17. The lifting mechanism of claim 16, wherein the sleeve is fabricated from a non-plastic material and the housing is fabricated from a plastic material.

18. The lifting mechanism of claim 16, wherein:
the piston comprises a piston rod and a flange adapted to seal against the sleeve; and
the housing defines an opening through which the piston rod may move, but through which the flange may not move.

19. The lifting mechanism of claim 16, wherein:
the housing has an interior height between a first location substantially near a bottom of the housing and a second location substantially near a top of the housing; and
the flange of the piston is operable to travel over the entire interior height depending on the fluid pressure within the sleeve, the flange of the piston being located at the first location substantially near the bottom of the housing when the fluid pressure within the sleeve is at its minimum, the flange of the piston being located at the second location substantially near the top of the housing when the fluid pressure within the sleeve is at its maximum.

20. The lifting mechanism of claim 16, wherein the housing comprises one or more inlets positioned such that a fluid may be pumped through the inlets into the substantially fluid-tight enclosure.

21. The lifting mechanism of claim 14, wherein the piston comprises a flange adapted to seal against the sleeve and the lifting mechanism further comprises a piston ring configured to be positioned around a perimeter of the flange to assist in forming a substantially fluid-tight seal between the flange and the sleeve.

22. The lifting mechanism of claim 14, wherein the piston defines a cavity fluidly coupled to an interior of the sleeve and extending through the piston.

23. The lifting mechanism of claim 22, further comprising an elastic member positioned in the cavity and coupled to the piston, the elastic member operable to retract the piston in response to a decrease in fluid pressure within the sleeve.

24. The tilling mechanism of claim 23, wherein the elastic member comprises a spring.

25. The lifting mechanism of claim 23:
wherein the housing has an interior height between a first location substantially near a bottom of the housing and a second location substantially near a top of the housing; and
wherein, as a result of the elastic member positioned within the cavity of the piston, the piston is operable to travel over the entire interior height depending on the fluid pressure within the sleeve, the piston being located at the first location substantially near the bottom of the housing when the fluid pressure within the sleeve is at its minimum, the piston being located at the second location substantially near the top of the housing when the fluid pressure within the sleeve is at its maximum.

26. The lifting mechanism of claim 23, wherein:
the housing has a height;
the piston has a maximum amount of extension from the housing; and
the lifting mechanism has a maximum height that is substantially equivalent to the height of the housing plus the maximum amount of extension of the piston.

27. A lifting mechanism for use with an ambulatory traction device, the lifting mechanism configured to be coupled between two supports of the traction device such that a joint of the user is positioned between the supports, the lifting mechanism operable to apply a decompressive force to the joint when the supports are positioned on the user's body, the lifting mechanism comprising:
a sleeve operable to contain a fluid;
a piston configured to move within the sleeve in response to an increase in fluid pressure within the sleeve, the piston having a flange adapted to seal against the sleeve, the piston defining a cavity fluidly coupled to an interior of the sleeve and extending through the piston including the flange;
a housing conformed to the sleeve and preventing the flange of the piston from exiting the sleeve, the housing having an interior height between a first location substantially near a bottom of the housing and a second location substantially near a top of the housing, the housing, sleeve, and flange of the piston collectively forming a substantially fluid-tight enclosure; and an elastic member coupled to the piston and positioned within the cavity of the piston including the flange, the elastic member operable to retract the piston in response to a decrease in fluid pressure within the sleeve;

the piston being operable as a result of the elastic member positioned within the cavity of the piston including the flange to travel over the entire interior height of the housing depending on the fluid pressure within the sleeve, the flange of the piston being located at the first location substantially near the bottom of the housing when the fluid pressure within the sleeve is at its minimum, the flange of the piston being located at the second location substantially near the top of the housing when the fluid pressure within the sleeve is at its maximum.

28. The lifting mechanism of claim 27, wherein the ambulatory traction device is an ambulatory spinal traction device, the supports are support belts, and the joint comprises at least a portion of the user's spine.

29. The lifting mechanism of claim 27, wherein the elastic member comprises a spring.

30. The lifting mechanism of claim 27, wherein:
the piston has a maximum amount of extension from the housing; and
the lifting mechanism has a maximum height that is substantially equivalent to the interior height of the housing plus the maximum amount of extension of the piston.

31. The lifting mechanism of claim 27, wherein the sleeve and the flange of piston each have substantially elliptical, non-circular cross-sections.

32. A lifting mechanism for use with an ambulatory traction device, the lifting mechanism configured to be coupled between two supports of the traction device such that a joint of the user is positioned between the supports, the lifting mechanism operable to apply a decompressive force to the joint when the supports are positioned on the user's body, the lifting mechanism comprising:

a sleeve operable to contain a fluid;

a piston configured to move within the sleeve in response to an increase in fluid pressure within the sleeve, the piston having a flange adapted to seal against the sleeve, the piston defining a cavity fluidly coupled to an interior of the sleeve and extending through the piston including the flange;

a housing conformed to the sleeve and preventing the flange of the piston from exiting the sleeve, the housing having an interior height between a first location substantially near a bottom of the housing and a second location substantially near a top of the housing, the housing, sleeve, and flange of the piston collectively forming a substantially fluid-tight enclosure; and means, positioned within the cavity of the piston including the flange, for retracting the piston in response to a decrease in fluid pressure within the sleeve;

the piston being operable as a result of the means for retracting to travel over the entire interior height of the housing depending on the fluid pressure within the sleeve, the flange of the piston being located at the first location substantially near the bottom of the housing when the fluid pressure within the sleeve is at its minimum, the flange of the piston being located at the second location substantially near the top of the housing when the fluid pressure within the sleeve is at its maximum.

33. An ambulatory traction device, comprising:

a first support belt configured to be positioned on a user's body, the first support belt comprising a plurality of first notches fanned in the first belt, each first notch configured to receive and secure a first clip of a lifting mechanism, the first support belt comprising a plurality of first semicircular slots formed in the first support belt, each first semicircular slot being curved in a first direction away from the lifting mechanism and at least partially surrounding a corresponding first notch;

a second support belt configured to be positioned on the user's body spaced apart from the first support such that a joint of the user's body is positioned between the first and second supports, the second support belt comprising a plurality of second notches formed in the second belt, each second notch configured to receive and secure a second clip of a lifting mechanism, the second support belt comprising a plurality of second semicircular slots formed in the second support bolt, each second semicircular slot being curved in a first direction away from the lifting mechanism and at least partially surrounding a corresponding second notch; and a plurality of lifting mechanisms coupled between the support belts and operable to apply a decompressive force to the joint when the support belts are positioned on the user's body, each lifting mechanism comprising:

a first clip located near a first end of the lifting mechanism and configured to be inserted through and secured to the first support belt using one of the first notches, the corresponding first semicircular slot of the first support belt allowing the first end of the lifting mechanism to rotate generally transverse to a surface of the first support belt adjacent the user's body; and a second clip located near a second end of the lifting mechanism and configured to be inserted through and secured to the second support belt using one of the second notches, the corresponding second semicircular slot of the second support belt allowing the second end of the lifting mechanism to rotate generally transverse to a surface of the second support belt adjacent the user's body, the first and second semicircular slots being configured such that rotation of the first end of the lifting mechanism generally transverse to the surface of the first support belt towards or away from the user requires rotation of the second end of the lifting mechanism generally transverse to the surface of the second support belt away from or towards the user, respectively.

34. The device of claim 33, wherein the device is an ambulatory spinal traction device and the joint comprises at least a portion of the user's spine.

35. The device of claim 33, wherein the first and second notches each comprise a substantially semi-circular shaped side curving in a direction generally away from the corresponding lifting mechanism.

36. The device of claim 33, wherein each slot is enlarged into a substantially circular opening at each of its ends.

37. The device of claim 33, wherein the lifting mechanism further comprises:

a sleeve having a non-circular cross-section and operable to contain a fluid;

a piston configured to move within the sleeve in response to an increase in fluid pressure within the sleeve, the piston comprising a noncircular flange adapted to seal against the sleeve; and a housing conformed to the sleeve and preventing the flange of the piston from exiting the sleeve in response to an increase in fluid pressure within the sleeve, the sleeve, housing, and flange collectively forming a substantially fluid-tight enclosure.

38. A lifting mechanism for use with an ambulatory traction device, the lifting mechanism configured to be coupled between two supports of the traction device such that a joint of a user is positioned between the supports, the lifting mechanism operable to apply a decompressive force to the joint when the supports are positioned on the user's body, the lifting mechanism comprising:

a sleeve having a non-circular cross-section and operable to contain a fluid;

a piston comprising a non-circular flange configured to be positioned inside of and to move within the sleeve in response to fluid pressure being applied against the flange;

a housing bottom comprising a seal; and a housing top coupled to the housing bottom to define a housing conformed to the sleeve and preventing the flange from exiting the sleeve, coupling of the housing top to the housing bottom urging the sleeve into a sealing relationship with the seal of the housing bottom such that the sleeve, housing, and flange thereafter collectively form a substantially fluid-tight enclosure.

39. The lifting mechanism of claim 38, wherein the sleeve is fabricated from a non-plastic material and the housing is fabricated from a plastic material.

40. The lifting mechanism of claim 38, wherein the housing comprises one or more inlets, the inlets positioned such that air may be pumped through the inlets into the substantially fluid-tight enclosure.

41. The lifting mechanism of claim 38, wherein the elastic member comprises a spring.

42. The lifting mechanism of claim 38, wherein:

the housing has an interior height between a first location substantially near a bottom of the housing and a second location substantially near a top of the housing; and the flange of the piston is operable to travel over the entire interior height depending on the fluid pressure within the sleeve, the flange of the piston being located at the first location substantially near the bottom of the housing when the fluid pressure within the sleeve is at its minimum, the flange of the piston being located at the second location substantially near the top of the housing when the fluid pressure within the sleeve is at its maximum.

43. The lifting mechanism of claim 38, wherein:

the piston further comprises a piston rod defining a cavity fluidly coupled to an interior of the sleeve and extending through the flange of the piston;

the housing defines an opening through which the piston rod may move, but through which the flange may not move; and the lifting mechanism further comprises an elastic member positioned in the cavity of the piston rod, the elastic member coupled between the piston rod and the housing and extending through the flange, the elastic member operable to retract the piston in response to a decrease in fluid pressure within the sleeve.

44. The lifting mechanism of claim 43, wherein:

the housing has a height;

the piston rod has a maximum amount of extension from the housing; and the lifting mechanism has a maximum height that is substantially equivalent to the height of the housing plus the maximum amount of extension of the piston rod.

\* \* \* \* \*

UNITED STATES PATENT AND TRADEMARK OFFICE
CERTIFICATE OF CORRECTION

PATENT NO. : 6,776,767 B2
DATED : August 17, 2004
INVENTOR(S) : Reinecke, Steven M., et al.

It is certified that error appears in the above-identified patent and that said Letters Patent is hereby corrected as shown below:

Column 1,
Line 30, delete "suffers" and insert in lieu thereof -- sufferers --;

Column 3,
Line 2, delete "a" and insert in lieu thereof -- an -- ;

Column 5,
Line 39, delete "elate" and insert in lieu thereof -- plate --;
Line 56, delete "elate" and insert in lieu thereof -- plate --;

Column 12,
Line 36, delete "torn" and insert in lieu thereof -- turn --;

Column 14,
Line 10, delete "users" and insert in lieu thereof -- user's --;

Column 15,
Line 2, delete "refract" and insert in lieu thereof -- retract --;

Column 16,
Line 25, delete "tilling" and insert in lieu thereof -- lifting --;

Column 18,
Line 7, delete "fanned" and insert in lieu thereof -- formed --.

Signed and Sealed this

Fourteenth Day of December, 2004

JON W. DUDAS
*Director of the United States Patent and Trademark Office*